United States Patent
Hugo et al.

(10) Patent No.: US 7,323,597 B2
(45) Date of Patent: *Jan. 29, 2008

(54) METHOD FOR THE PRODUCTION OF DIAMINOXYLENE BY CONTINUOUS HYDROGENATION OF LIQUID PHTHALONITRILE

(75) Inventors: Randolf Hugo, Dirmstein (DE); Kirsten Wenz, Mannheim (DE); Sabine Jourdan, Mannheim (DE); Thomas Preiss, Weisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/571,260

(22) PCT Filed: Sep. 9, 2004

(86) PCT No.: PCT/EP2004/010062

§ 371 (c)(1),
(2), (4) Date: Mar. 9, 2006

(87) PCT Pub. No.: WO2005/026098

PCT Pub. Date: Mar. 24, 2005

(65) Prior Publication Data

US 2007/0027345 A1   Feb. 1, 2007

(30) Foreign Application Priority Data

Sep. 10, 2003   (DE)   ................................ 103 41 612

(51) Int. Cl.
*C07C 211/00* (2006.01)

(52) U.S. Cl. ..................................................... 564/336
(58) Field of Classification Search ................. 564/336
See application file for complete search history.

(56) References Cited

U.S. PATENT DOCUMENTS 3,069,469 A   12/1962   Wilkes
3,972,938 A   8/1976   Voges et al.

(Continued)

FOREIGN PATENT DOCUMENTS

DE   1 119 285   12/1961

(Continued)

OTHER PUBLICATIONS

"Process Handbook, edited by The Japan Petroleum Institute (1976)", (English translation of relevant portions thereof).

*Primary Examiner*—Yvonne Eyler
*Assistant Examiner*—Kellette Gale
(74) *Attorney, Agent, or Firm*—Connolly Bove Lodge and Hutz

(57) ABSTRACT

A process for preparing xylylenediamine by continuously hydrogenating liquid phthalonitrile over a heterogeneous catalyst in the presence of liquid ammonia in a reactor, in which a portion of the reactor effluent is recycled as a liquid circulation stream continuously to the reactor inlet (circulation mode), in which a stream of a phthalonitrile melt in liquid form is conducted by means of a mixer unit into the circulation stream around the hydrogenation reactor, the phthalonitrile conversion in the reactor on single pass being greater than 99%, and the circulation stream consisting to an extent of greater than 93% by weight of liquid ammonia and xylylenediamine and not comprising any further solvent for phthalonitrile.

21 Claims, 2 Drawing Sheets

U.S. PATENT DOCUMENTS 4,482,741 A * 11/1984 Kurek .................. 564/415
6,476,269 B2 * 11/2002 Nakamura et al. ......... 564/388

FOREIGN PATENT DOCUMENTS

| DE | 2 164 169 | 7/1972 |
| DE | 102004042947.2 | 9/2004 |
| EP | 1 193 244 | 4/2002 |
| EP | 1 193 247 | 4/2002 |
| EP | 1 279 661 | 1/2003 |
| GB | 852972 | 11/1960 |
| JP | 2003 327563 | 11/2003 |

* cited by examiner

Scheme: MXDA - Hydrogenation of IPN to MXDA

Mixer nozzle radial feed:

or tangential feed:

or

METHOD FOR THE PRODUCTION OF DIAMINOXYLENE BY CONTINUOUS HYDROGENATION OF LIQUID PHTHALONITRILE

CROSS REFERENCE TO RELATED APPLICATION

The present application is a National Stage application of PCT/EP2004/010062, filed Sep. 9, 2004, which claims priority from German Patent Application Nos. DE 103 41 612.9, 103 41 633.1, 103 41 632.3, 103 41 615.3, 103 41 613.7, and 103 41 614.5, all filed on Sept. 10, 2003 and German Patent Application No. DE 10 2004 042954.5 filed on Sep. 2, 2004.

DESCRIPTION

The present invention relates to a process for preparing xylylenediamine by continuously hydrogenating liquid phthalonitrile over a heterogeneous catalyst in the presence of liquid ammonia in a reactor, in which a portion of the reactor effluent is recycled as a circulation stream continuously to the reactor inlet (circulation mode).

Xylylenediamine (bis(aminomethyl)benzene) is a useful starting material, for example, for the synthesis of polyamides, epoxy hardeners or as an intermediate for preparing isocyanates.

The term "xylylenediamine" (XDA) embraces the three isomers, ortho-xylylenediamine, meta-xylylenediamine (MXDA) and para-xylylenediamine.

The term "phthalonitrile" (PN) embraces the three isomers, 1,2-dicyanobenzene=o-phthalonitrile, 1,3-dicyanobenzene=isophthalonitrile=IPN and 1,4-dicyanobenzene=terephthalonitrile.

The phthalonitriles are solids (for example, isophthalonitrile (IPN) melts at 161° C.) and have relatively poor solubilities in organic solvents.

The two-stage synthesis of xylylenediamine by ammoxidation of xylene and subsequent hydrogenation of the resulting phthalonitrile is known. Unconverted dinitriles are very difficult to remove distillatively from the XDA.

U.S. Pat. No. 4,482,741 (UOP Inc.) describes the hydrogenation of PN in the presence of ammonia, a specific catalyst and XDA as a solvent.

In MXDA, the solubility of IPN at 70° C. is approx. 20% by weight.

EP-A2-1 193 247 and EP-A1-1 279 661 (both Mitsubishi Gas Chem. Comp.) relate, respectively, to a process for purifying isophthalonitrile (IPN) and to a process for preparing pure XDA.

EP-A2-1 193 244 (Mitsubishi Gas Chem. Comp.) describes a process for preparing XDA by hydrogenating phthalonitrile which is synthesized in a preceding stage by ammoxidation of xylene, wherein the vaporous product of the ammoxidation stage is contacted directly with a liquid organic solvent (quench) and the resulting quench solution or suspension is fed to the hydrogenation.

Preferred organic solvents are $C_6$-$C_{12}$ aromatic hydrocarbons, such as xylene and pseudocumene (column 6, paragraph [0027] and [0028]).

U.S. Pat. No. 3,069,469 (California Research Corp.) teaches aromatic hydrocarbons, xylene, dioxane and aliphatic alcohols as solvents for the hydrogenation of aromatic nitrites such as PN.

DE-A-21 64 169 (Mitsubishi Gas Chemical Co., Inc.) describes, on page 6, last paragraph, the hydrogenation of IPN to meta-XDA in the presence of an Ni and/or Co catalyst in ammonia as a solvent.

GB-A-852,972 (equivalent: DE-A-11 19 285) (BASF AG) discloses the use of ammonia and XDA as a solvent in the hydrogenation of PN. The reactant solution is prepared starting from solid PN in an extra step in a separate vessel (cf. page 2, lines 119-120).

JP-A-2003-327563 (Mitsubishi Gas Chem. Co., Inc.) relates to a process for the fixed bed hydrogenation of aromatic dinitriles which are used as 1-10% by weight solutions.

The six German patent applications having the reference numbers 10341615.3, 10341632.3, 10341614.5, 10341633.1, 10341612.9 and 10341613.7 (BASF AG) of Sept. 10, 2003 each relate to processes for preparing XDA.

A parallel German Patent Application No. 102004042947.2 having the same filing date (BASF AG) relates to a process for preparing XDA by continuously hydrogenating liquid PN over a heterogeneous catalyst in the presence of liquid ammonia in a reactor, wherein a stream of a phthalonitrile melt is conducted in liquid form by means of a mixer unit into a stream of liquid ammonia and the liquid mixture is fed into the hydrogenation reactor.

In the different processes for preparing phthalonitrile, it is obtained as a solid or dissolved in a solvent, for example pseudocumene, or as a melt. The handling of solids is typically difficult and laborious. Owing to the low solubility of phthalonitrile in solvents such as o-xylene, m-xylene, p-xylene, pseudocumene, mesitylene, ethylbenzene or methylpyridine, the further processing in a solvent requires very large amounts of solvent which generally have to be removed distillatively after the hydrogenation, which requires large apparatus and a high energy input corresponding to the large mass flow rates. Alternatively, an extraction of the PN with water with subsequent distillation is possible. Here too, the energy input is large, since the water has to be distilled off and the solvent regenerated, at least partially.

DETAILED DESCRIPTION OF EMBODIMENTS OF THE INVENTION

Figure 1:
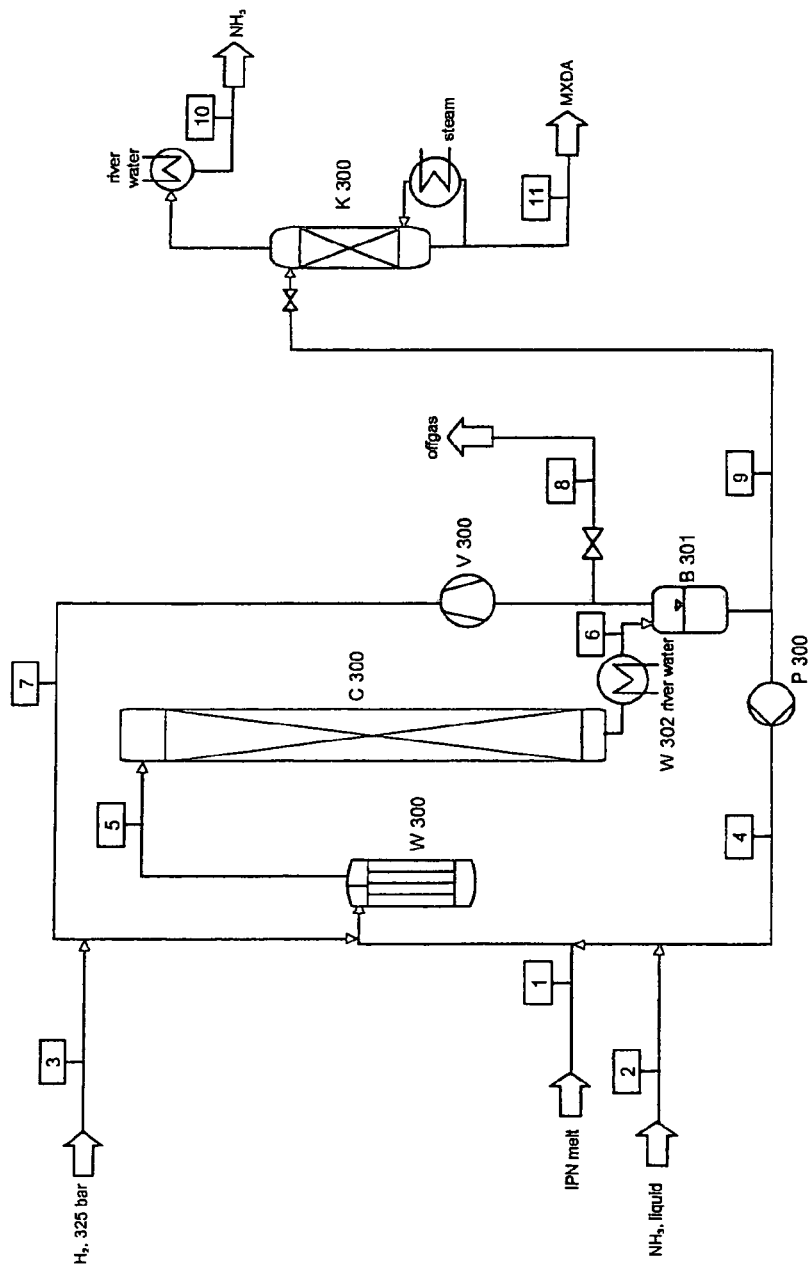
FIG. 1 shows a representative schematic of a possible arrangement of a hydrogenation reactor with a circulation system, heat exchangers, and MXDA workup.

It is an object of the present invention to find an improved economically viable process for preparing xylylenediamine, especially meta-xylylenediamine, with high selectivity, yield and space-time yield (STY), which enables reduced-scale and/or fewer apparatuses and machines at throughputs comparable to the prior art owing to reduced streams, especially solvent streams, including recycle streams.

Accordingly, a process has been found for preparing xylylenediamine by continuously hydrogenating liquid phthalonitrile over a heterogeneous catalyst in the presence of liquid ammonia in a reactor, in which a portion of the reactor effluent is recycled as a liquid circulation stream continuously to the reactor inlet (circulation mode), which comprises conducting a stream of a phthalonitrile melt in liquid form by means of a mixer unit into the circulation stream around the hydrogenation reactor, the phthalonitrile conversion in the reactor on single pass being greater than 99%, and the circulation stream consisting to an extent of greater than 93% by weight of liquid ammonia and xylylenediamine and not comprising any further solvent for phthalonitrile.

The process according to the invention preferably finds use for preparing meta-xylylenediamine (MXDA) by hydrogenating isophthalonitrile (IPN), which has been synthesized in particular in a preceding stage by ammoxidation of meta-xylene.

The molten phthalonitrile may come, for example, from a quench connected downstream of an ammoxidation, an evaporative concentration stage or a distillation column, and the phthalonitrile may, for example, in each case be removed as a melt via the bottom of these thermal separation apparatuses, as described, for example, in German patent application no. 10341633.1 of Sep. 10, 2003 (BASF AG).

Alternatively, it is also possible in the process according to the invention to use molten PN present beforehand as a solid. The melting may be effected, for example, by means of an extruder.

The advantage of metering the PN as a melt into the circulation stream around the hydrogenation reactor is the quite high dilution in the course of metered addition, rapid cooling after mixing and thus prevention of reaction between nitrile and product amine. This reduces by-product formation.

The high dilution is also advantageous during the reaction, since the heat of reaction can thus be removed convectively (i.e. with the heated reactor effluent). This allows the temperature increase in the reactor to be restricted. The adjustment of the reactor feed temperature and the size of the circulation stream allows the temperature profile in the reactor to be influenced. A lower reactor temperature leads to a further increase in the selectivity.

The dilution of the PN with the circulation stream achieves a high ammonia concentration based on PN, which in turn has a favorable effect on the selectivity. Nevertheless, only a small fresh $NH_3$ stream is needed and only a small ammonia column for the recovery and recycling of the ammonia removed from the reaction circuit together with the xylylenediamine. Without a circulation stream, more ammonia would have to be fed in and then distilled off again to establish the same reaction conditions.

The feeding and dissolution of the phthalonitrile melt in the circulation solution (in the circulation stream) requires a mixer unit, preferably a mixer nozzle, which can be realized in the simplest case by a pipeline T-piece. The nozzle mouth preferably has a narrowing.

The streams are fed separately and are mixed and homogenized in the attached tube on the basis of the prevailing turbulence. Advantageously, a static mixer may additionally be connected downstream. However, no additional apparatus, for instance a stirred tank for the dissolution of (solid or liquid) phthalonitrile in a solvent, is required.

Preference is given to heating the mixer unit at the point of the phthalonitrile supply into the circulation stream to a temperature in the range from 1 to 40° C., preferably in the range from 5 to 25° C., above the melting point of the phthalonitrile used.

Preference is given to supplying the PN virtually at reactor pressure. Particular preference is given to feeding the PN in such a way that no evaporation sets in at the mixing temperature established, but rather the mixture remains liquid.

Particular preference is given to spraying the liquid phthalonitrile by means of a mixer nozzle as the mixer unit into the circulation stream.

Figure 2:
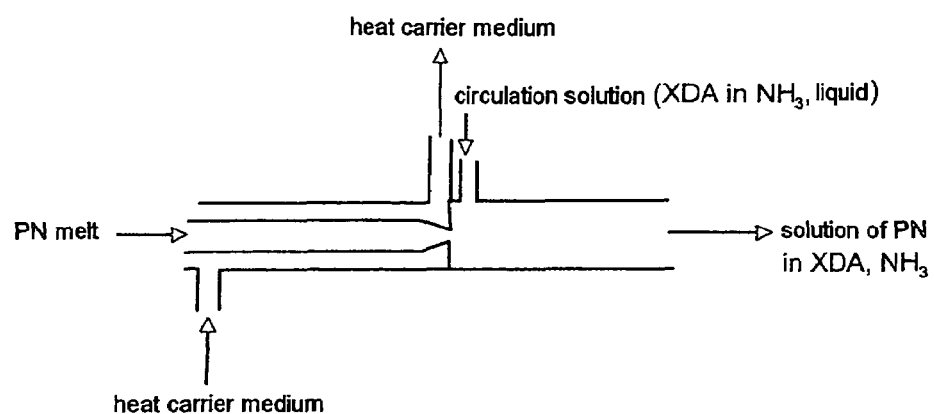
FIG. 2 shows a longitudinal-sectional view of a preferred embodiment of a mixer nozzle.

A preferred embodiment of the mixer nozzle is shown in FIG. 2 in the appendix. The mixer nozzle may be heated, for example, with steam, heat carrier oil or else electrically.

Figure 3:
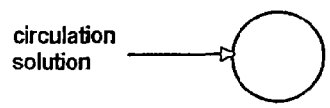
FIG. 3 shows a cross-sectional view of different alternatives of feeding the circulation solution into the mixer nozzle.
Figure 3:
Figure 3:
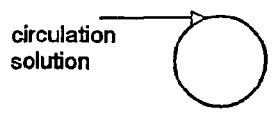
Figure 3:
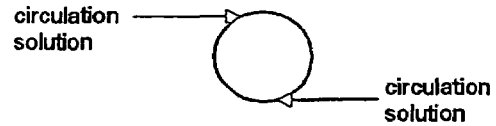

The circulation solution may be fed via one or more radially or tangentially mounted nozzles, for example as shown in FIG. 3.

It is important that there is a localized high flow rate (high impulse stream and turbulence), so that rapid mixing (homogenization) occurs. In the case of laminar flow, the mass transfer is insufficient for homogenization and the flows are only mixed inadequately (streaking).

Suitable mixer nozzles are described, for example, in Ullmann's Encyclopedia of Industrial Chemistry, 5th edition, Vol. B4, pages 565-569.

The phthalonitrile conversion in the hydrogenation reactor on single pass is preferably greater than 99.5%, particularly greater than 99.9%, in particular greater than 99.95%, very particularly greater than 99.97%. In the hydrogenation reactor, appropriate setting of the reaction conditions (pressure, temperature, molar ratios of PN, $NH_3$ and $H_2$, catalyst, mass flow rates, residence time in the reactor) allows virtually full conversion to be attained.

The liquid circulation stream consists preferably to an extent of greater than 94% by weight, in particular greater than 95% by weight, very particularly greater than 96% by weight, of liquid ammonia and xylylenediamine; the remainder is formed by secondary components.

Secondary components in the liquid circulation stream may be by-products formed in the reaction, and also dissolved gases and secondary components fed with the phthalonitrile, but not a further solvent, for example organic solvent, for phthalonitrile.

The circulation stream contains preferably in the range from 25 to 90% by weight, particularly from 30 to 70% by weight, in particular from 45 to 60% by weight, of liquid ammonia.

The portion of the liquid effluent which is recycled as a circulation stream continuously to the reactor inlet makes up preferably from 20 to 95% by weight, particularly from 50 to 92% by weight, in particular from 75 to 90% by weight, of the overall liquid reactor effluent.

The weight ratio of phthalonitrile feed stream to circulation stream is preferably in the range from 0.03 to 1.0, particularly in the range from 0.05 to 0.5, in particular in the range from 0.07 to 0.2.

The reaction temperature is preferably in the range from 40 to 150° C., more preferably from 60 to 135° C., in particular from 70 to 130° C.

The amount of the circulation stream and the reactor feed temperature are adjusted such that the reactor outlet temperature does not exceed the desired maximum value (for example 130° C.), since by-products are formed to an enhanced degree with increasing temperature. The reactor feed temperature is adjusted in such a way (for example by an additional heat carrier or, preferably, by suitably adjusting the temperature of the streams to be mixed), that the reaction proceeds sufficiently rapidly and full conversion is attained. Variation of the circulation mass flow rate thus makes it possible to adjust both inlet and outlet temperature of the reactor and adjust them optimally to the reactions proceeding, and thus to optimize the XDA yield.

The hydrogenation is carried out preferably at an absolute pressure in the range from 100 to 300 bar, in particular from 120 to 220 bar, very particularly from 150 to 200 bar.

For the hydrogenation, the catalysts and reactors known to those skilled in the art (especially tubular reactors or tube bundle reactors; fixed bed or suspension mode) may be employed.

In the fixed bed catalyst method, both the liquid phase and the trickle mode are possible. Preference is given to trickle mode.

Preference is given to operating the reactor adiabatically, while the heat of reaction which arises is removed via a cooler installed in the circulation system, and also optionally with the cycle gas used. This additionally increases the selectivity of the reaction by the further suppression of by-products.

Alternatively, it is also possible to use a cooled reactor, for example a tube bundle reactor.

Preference is given to catalysts which comprise cobalt and/or nickel and/or iron, as an unsupported catalyst or on an inert support.

Particular preference is given to carrying out the hydrogenation over a manganese-doped unsupported cobalt catalyst.

Suitable catalysts are for example, Raney nickel, Raney cobalt, unsupported cobalt catalyst, titanium-doped cobalt on support (JP-A-2002 205980), Ni on $SiO_2$ support (WO-A-2000/046179), Co/Ti/Pd on $SiO_2$ support (CN-A-1 285 343, CN-A-1 285 236) and nickel and/or cobalt on zirconium dioxide support (EP-A1-1 262 232).

Examples of further suitable catalysts can be found, for example, in the applications GB-A-852,972 (equivalent: DE-A-11 19 285) (BASF AG), DE-A-12 59 899 (BASF AG) and the U.S. Pat. No. 3,069,469 (California Research Corp.) and 4,482,741 (UOP Inc.).

Particularly preferred catalysts are the unsupported cobalt catalysts doped with Mn, P and alkali metal (Li, Na, K, Rb, Cs) which are disclosed in EP-A1-742 045 (BASF AG). Before the reduction with hydrogen, the catalytically active composition of these catalysts consists of from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, calculated in each case as the oxide.

Further suitable catalysts are the catalysts disclosed in EP-A-963 975 (BASF AG), whose catalytically active composition before treatment with hydrogen contains from 22 to 40% by weight of $ZrO_2$,
from 1 to 30% by weight of oxygen compounds of copper, calculated as CuO,
from 15 to 50% by weight of oxygen compounds of nickel, calculated as NiO, where the molar Ni:Cu ratio is greater than 1,
from 15 to 50% by weight of oxygen compounds of cobalt, calculated as CoO,
from 0 to 10% by weight of oxygen compounds of aluminum and/or manganese, calculated as $Al_2O_3$ or $MnO_2$,
and no oxygen compounds of molybdenum,
for example the catalyst A disclosed in loc. cit., page 17, with the composition of 33% by weight of Zr, calculated as $ZrO_2$, 28% by weight of Ni, calculated as NiO, 11% by weight of Cu, calculated as CuO and 28% by weight of Co, calculated as CoO, the catalysts disclosed in EP-A-696 572 (BASF AG), whose catalytically active composition before the reduction with hydrogen contains from 20 to 85% by weight of $ZrO_2$, from 1 to 30% by weight of oxygen compounds of copper, calculated as CuO, from 30 to 70% by weight of oxygen compounds of nickel, calculated as NiO, from 0.1 to 5% by weight of oxygen compounds of molybdenum, calculated as $MoO_3$, and from 0 to 10% by weight of oxygen compounds of aluminum and/or manganese, calculated as $Al_2O_3$ or $MnO_2$, for example the catalyst disclosed in loc. cit., page 8, with the composition of 31.5% by weight of $ZrO_2$, 50% by weight of NiO, 17% by weight of CuO and 1.5% by weight of $MoO_3$,
and the catalysts described in WO-A-99/44984 (BASF AG) and containing (a) iron or a compound based on iron or mixtures thereof, (b) from 0.001 to 0.3% by weight based on (a) of a promoter based on 2, 3, 4 or 5 elements selected from the group of Al, Si, Zr, Ti, V, (c) from 0 to 0.3% by weight based on (a) of a compound based on an alkali metal and/or alkaline earth metal, and (d) from 0.001 to 1% by weight based on (a) of manganese.

The process according to the invention can be performed, for example, as follows:

FIG. 1 shows one possible arrangement of the hydrogenation reactor with circulation system and heat transferers. The phthalonitrile melt is fed as a stream [1] of the hydrogenation stage and mixed with the circulation stream [4]. Ammonia [2] is added in liquid form. This may be done either upstream of the mixing point with the phthalonitrile melt (as shown in FIG. 1) or downstream thereof Hydrogen [3] and any cycle gas are fed in and heated to the desired reactor feed temperature by means of an optional heat transferer. Gas and liquid may also be fed [5] to the reactor separately. Preference is given to setting the temperature of the streams to be mixed by means of heat transferers in such a way that no farther heat transferer is required after mixing. Gas and liquid are preferably fed separately to the hydrogenation reactor. In the reactor, the hydrogenation proceeds virtually quantitatively, so that virtually no phthalonitrile is present any longer in the reaction effluent [6]. The reaction effluent may then be cooled, and gas and liquid are separated under pressure in a high-pressure separator. The liquid is partly circulated without workup (stream [4]) and partly fed to workup (stream [9]). A portion of the gas is discharged [8] in order to prevent the accumulation of inerts (CO, $N_2$, $CH_4$, noble gases, etc.). The majority of the gas [7] is recycled to the reactor inlet via a compressor. In the event of not too high a pressure drop in the reactor, it is preferably also possible for this purpose to use an ejector jet nozzle ("water-jet pump"). Overall, the amount of cycle gas may be varied within wide ranges, for instance from several times the amount of fresh gas down to zero (method without cycle gas). The cycle gas mode is favorable in order to load the reactor on the gas side sufficiently for good mass transfer and in order to provide a sufficient entrainment stream for inert gases. In addition, a portion of the heat of reaction may be removed with the gas stream. With increasing temperature, an increasing amount of ammonia evaporates, which further enhances the cooling effect of the cycle gas. The reaction effluent (stream [9]) is then fed initially to a pressure distillation, in which liquid ammonia is obtained overhead (stream [10]) and substantially ammonia-free, crude xylylenediamine is obtained via the bottom (stream [11]), and the ammonia can be fed back to the hydrogenation stage in condensed form. The crude xylylenediamine is further purified, for example, by distillation.

In the process according to the invention, the larger the circulation stream is, the larger the weight ratio of the fresh feeds of dinitrile and ammonia (for example, according to FIG. 1, the ratio of stream [1] to stream [2]) selected may be.

The weight ratio of dinitrile to ammonia is preferably from 1:0.5 to 1:10, preferentially from 1:0.6 to 1:5, more preferably from 1:0.9 to 1:3.5.

Isolation of the XDA:

After the hydrogenation, the ammonia used is removed, for example distilled off.

Preference is given to purifying the xylylenediamine by distilling off relatively low-boiling by-products (at the same pressure) overhead and distillatively removing relatively high-boiling impurities via the bottom.

Particular preference is given to the method in which, after the hydrogenation, the ammonia and any low-boiling by-products are distilled off overhead and then relatively high-boiling impurities are removed from the xylylenediamine distillatively via the bottom.

In a particular embodiment, the removal of relatively low- and relatively high-boiling by-products may also be effected in a side draw or dividing wall column, in which pure xylylenediamine is obtained via a liquid or gaseous side draw.

Depending on the desired purity, the product (XDA) is additionally extracted with an organic solvent, preferably an aliphatic hydrocarbon, in particular a cycloaliphatic hydrocarbon, very particularly cyclohexane or methylcyclohexane. This purification by extraction may be effected, for example, according to DE-A-1 074 592 (BASF AG).

EXAMPLE 90 g/h of molten IPN (commercial, chip-form IPN which has been melted by heating to approx. 170° C.) was conducted into a circulation stream (approx. 1000 g/h) consisting of the liquid recycle stream of the reactor effluent and 90 g/h of fresh ammonia. The resulting reaction mixture was hydrogenated continuously in a tubular reactor over an unsupported cobalt catalyst at 90° C. and 200 bar. The removed portion of the reactor effluent was freed of the majority of the amount of ammonia in an ammonia column and analyzed by GC. At full conversion of the IPN used (i.e. conversion greater than 99.95%; no reactants detectable by GC), the selectivity was 93%.

In subsequent distillation steps, residual ammonia and low-boiling secondary components were first removed. After removing the high-boiling impurities via the bottom, MXDA was obtained as the top product of a distillation column in a purity of more than 99.9% by weight.

What is claimed is:

1. A process for preparing xylylenediamine comprising continuously hydrogenating liquid phthalonitrile over a heterogeneous catalyst in the presence of liquid ammonia in a reactor, in which a portion of the reactor effluent is recycled as a liquid circulation stream continuously to the reactor inlet (circulation mode), which comprises conducting a stream of a phthalonitrile melt in liquid form by means of a mixer unit into the circulation stream around the hydrogenation reactor, the phthalonitrile conversion in the reactor on single pass being greater than 99%, and the circulation stream consisting to an extent of greater than 93% by weight of liquid ammonia and xylylenediamine and not comprising any further solvent for phthalonitrile.

2. The process according to claim 1 comprising hydrogenating isophthalonitrile in order to prepare meta-xylyenediamine.

3. The process according to claim 1, wherein the mixer unit is heated at the point of the phthalonitrile supply into the circulation stream to a temperature in the range from 1 to 400° C. above the melting point of the phthalonitrile used.

4. The process according to claim 1, wherein the liquid phthalonitrile is sprayed into the circulation stream by means of a mixer nozzle as the mixer unit.

5. The process according to claim 1, wherein the phthalonitrile conversion in the hydrogenation reactor on single pass is greater than 99.5%.

6. The process according to claim 1, wherein the phthalonitrile conversion in the hydrogenation reactor on single pass is greater than 99.9%.

7. The process according to claim 1, wherein the circulation stream consists to an extent of greater than 94% by weight of liquid ammonia and xylylenediamine.

8. The process according to claim 1, wherein the circulation stream contains in the range from 25 to 90% by weight of liquid ammonia.

9. The process according to claim 1, wherein the portion of the liquid reactor effluent which is recycled as the circulation stream continuously to the reactor inlet makes up from 20 to 95% by weight of the overall liquid reactor effluent.

10. The process according to claim 1, wherein the weight ratio of phthalonitrile feed stream to circulation stream is in the range from 0.03 to 1.0.

11. The process according to claim 1, wherein the hydrogenation is carried out at a temperature in the range from 40 to 150° C.

12. The process according to claim 1, wherein the hydrogenation is carried out at an absolute pressure in the range from 100 to 300 bar.

13. The process according to claim 1, wherein the hydrogenation is carried out over a catalyst comprising Ni, Co and/or Fe, as an unsupported catalyst or on an inert support.

14. The process according to claim 1, wherein the hydrogenation is carried out over a manganese-doped unsupported cobalt catalyst.

15. The process according to claim 1, wherein the catalyst is disposed as a fixed bed in a tubular reactor or tube bundle reactor.

16. The process according to claim 1, wherein the reactor is operated in trickle mode.

17. The process according to claim 1, wherein the reactor is operated adiabatically.

18. The process according to claim 1, wherein heat is withdrawn from the circulation stream in a cooler.

19. The process according to claim 1, wherein the xylylenediamine is purified after the hydrogenation by distilling off the ammonia and also any relatively low-boiling by-products overhead and distillatively removing relatively high-boiling impurities via the bottom.

20. The process according to claim 19, wherein the xylylenediamine is extracted after the distillation with an organic solvent for further purification.

21. The process according to claim 20, wherein cyclohexane or methylcyclohexane are used for the extraction.

* * * * *